(12) United States Patent
Shiekhattar

(10) Patent No.: US 7,691,976 B2
(45) Date of Patent: Apr. 6, 2010

(54) BRAF35 PROTEIN AND BRCA2/BRAF35 COMPLEX AND METHODS OF USE

(75) Inventor: Ramin Shiekhattar, Philadelphia, PA (US)

(73) Assignee: The Wistar Institute, Philadelphia, PA (US)

( * ) Notice: Subject to any disclaimer, the term of this patent is extended or adjusted under 35 U.S.C. 154(b) by 967 days.

(21) Appl. No.: 10/416,387

(22) PCT Filed: Nov. 13, 2001

(86) PCT No.: PCT/US01/47101

§ 371 (c)(1),
(2), (4) Date: Oct. 10, 2003

(87) PCT Pub. No.: WO02/38795

PCT Pub. Date: May 16, 2002

(65) Prior Publication Data

US 2004/0053347 A1  Mar. 18, 2004

(51) Int. Cl.
*C07K 14/00* (2006.01)
*C07K 17/00* (2006.01)
*A61K 38/16* (2006.01)
*G01N 33/00* (2006.01)
*G01N 1/00* (2006.01)
*G01N 1/18* (2006.01)

(52) U.S. Cl. .................. 530/358; 530/350; 530/361; 436/86; 436/174; 436/177; 436/178

(58) Field of Classification Search .................. 530/350, 530/358, 361; 436/86, 174, 177, 178
See application file for complete search history.

(56) References Cited

OTHER PUBLICATIONS

GenCore database sheets. Alignment between nucleic acid sequence of Sumoy et al. (Cytogenet. Cell Genet. 88 (1-2): 62-67, Jun. 2000) and Applicant's SEQ ID No. 1, 4 sheets.*
Sumoy et al. Hov6 20A & HMG 20B Map to Human Chromosomes 15q24 & 19p 13.3 & Constitute a Distinct Class of HMG-Box Genes With Ubiquitous Expression. Cytogenetics & Cell Genetics 88:62-67 (2000).*
Ohno et al. A nuclear cap binding protein from Hela cells. Nucleic Acids Research 18(23): 6989-6995, 1990.*
Marmorstein et al. The BRCA2 gene product functionally interacts with p53 and RAD51. Proc. Natl. Acad. Sci. USA 95: 13869-13874, Nov. 1998.*
Marmorstein et al., "A Human BRCA2 Complex Containing a Structural DNA Binding Component Influences Cell Cycle Progression", Cell 2001 104:247-257.

* cited by examiner

*Primary Examiner*—Alana M Harris
(74) *Attorney, Agent, or Firm*—Licata & Tyrrell P.C.

(57) ABSTRACT

An isolated nucleic acid sequence of BRAF35 and polypeptides encoded thereby are provided, as well as a multiprotein complex, and an antibody capable of binding selectively to the BRAF35 protein. Related agents and compositions which modulate interaction between BRCA2 and BRAF35 and methods of their use for screening for the BRCA2 protein, suppressing tumors and identifying DNA damage in cells indicative of a risk for developing cancer are also provided.

1 Claim, 1 Drawing Sheet

FIGURE 1

```
  1  MSHGPKQPGAAAAPAGGKAPGQHGGFVVTVKQERGEGPRAGEKGSHEEEP
 51  VKKRGWPKGKRKKILPNGPKAPVTGYVRFLNERREQIRTRHPDLPFPEI
101  TKMLGAEWSKLQPTEKQRYLDEAEREKQQYMKELRAYQQSEAYKMCTEKI
151  QEKKIKKEDSSSGLMNTLLNGHKGGDCDGFSTFDVPIFTEEFLDQNKARE
201  AELRRLRKMNVAFEEQNAVLQRHTQSMSSARERLEQELALEERRTLALQQ
251  QLQAVRQALTASFASLPVPGTGETPTLGTLDFYMARLHGAIERDPAQHEK
301  LIVRIKEILAQVASEHL
```

BRAF35 PROTEIN AND BRCA2/BRAF35 COMPLEX AND METHODS OF USE

BACKGROUND OF THE INVENTION

Mutations of one copy of the BRCA2 gene predisposes humans to breast cancer (Wooster et al., Nature, 1995. 378: 789-792, Tavtigian et al., Nat. Genetic, 1996. 12:333-337). Breast tumors from predisposed individuals often display mutations in both alleles suggesting that BRCA2 serves as a tumor suppressor (Collins et al., Oncogene 1995. 10:1673-1675, Gudmundson et al., Cancer Research 1995. 55:4830-4832). In addition, deleterious alleles of BRCA1 and BRCA2 are responsible for almost all familial ovarian cancer, and deleterious alleles of BRCA2 are also involved in hereditary male breast cancer (Wooster et al., 1995, Tavtigian et al., Nat. Genetic, 1996. 12:333-337, Miki et al., Science 1994. 266: 66-71). BRCA2 encodes a large protein of about 390 kDa which does not possess any obvious homology with sequences available in the public database (Tavtigian et al., Nat. Genetic, 1996. 12:333-337).

Recently, in vitro transactivation assays have suggested a role for the amino-terminal domain of BRCA2 in transcriptional regulation (Milner et al., Nature 1997. 386: 772-773). However, most of the current data point to a role for the BRCA2 protein in DNA repair. It has been reported that the BRCA2 protein interacts with RAD51 (Marmorstein et al., Natl. Acad Sci. 1998. USA 95: 13869-13874, Chen et al., Proc. Natl. Acad. Sci. 1998. USA 95: 5287-5292, Mizuta et al., Proc. Natl. Acad. Sci. 1997. USA 94: 6927-6932), the human homolog of Escherichia coli recA (Shinohara et al., Cell 1992. 69:457-470). RAD51 is the hallmark of homologous recombination, suggesting a function for BRCA2 in recombination or double-strand break DNA repair. It has also been shown that murine embryos with a targeted disruption of BRCA2 displayed sensitivity to ionizing radiation (Sharan et al., Nature 1997. 386:804-810). Mouse embryo fibroblasts (MEFs) with a targeted disruption of BRCA2 exon 11 displayed increased sensitivity to ultraviolet light and methyl methanesulfonate (MMS) (Patel et al., Mol. Cell, 1998. 1:347-357).

To determine the role for the BRCA2 protein in cancer predisposition, attempts have been made to analyze the induction of tumors in mice with a targeted deletion in BRCA2. However, contrary to expectations, mouse strains heterozygous for mutations in BRCA2 failed to show a predisposition to tumor formation (Ludwig et al., Genes Dev., 1997. 11:1226-1241, Sharan et al., Nature, 1997. 386:804-810, Suzuki et al., Genes Dev., 1997. 11:1242-1252, Connor et al., Nat. Genet., 1997. 17:423-430). Homozygosity caused early embryonic lethality at day 7.5-8.5 and was accompanied by retarded embryonic growth in vivo and in vitro (Ludwig et al., Genes Dev., 1997. 11:1226-1241, Sharan et al., Nature, 1997. 386:804-810, Suzuki et al., Genes Dev., 1997. 11:1242-1252). Embryonic survival was prolonged to day 10.5 when the analysis was performed with BRCA2 homozygous mouse with a p53-null background (Ludwig et al., Genes Dev., 1997. 11:1226-1241). It has also been shown that some animals with a homozygous deletion of exon 11 survive to maturity and succumb to thymic lymphomas (Friedman et al., Cancer Research, 1998. 58:1338-1343). Human BRCA2 exon 11 is composed of eight internal repeats known as the "BRC repeats" that are conserved in all mammalian BRCA2 proteins that have been sequenced (Koonin et al., Nat. Genet., 1996. 13:266-268, Bork et al., Nat. Genet., 1996. 13:22-23).

SUMMARY OF INVENTION

An object of the present invention is to provide an isolated nucleic acid sequence of BRAF35 and polypeptides encoded thereby. A further object of this invention is to provide a multiprotein complex comprising BRAF35 and antibodies preferably polyclonal or monoclonal antibodies, which bind selectively to the BRAF35 protein. Antibodies of the present invention can be detectably labeled and used to detect cancers, particularly ovarian and breast cancer. In addition, these antibodies can be used to detect BRAF35 DNA damage in cells.

This invention also provides agents and compositions which modulate interaction between BRCA2 and BRAF35 and methods of their use for screening for the BRCA2 protein and suppressing tumors.

BRIEF DESCRIPTION OF THE FIGURES

FIG. 1 shows the primary amino-acid sequence of BRAF35 (SEQ ID NO: 1). The conserved HMG domain is single underlined and the kinesin-like domain is double underlined.

DETAILED DESCRIPTION OF THE INVENTION

Chromosome condensation is a cellular process in which entangled chromatin fibers are resolved and packaged into physically separate compact structures, the mitotic chromosomes. This process is prerequisite for the subsequent segregation of chromosomes in anaphase and is essential for maintaining the integrity of genetic information throughout mitosis. Recent genetic and biochemical studies in eukaryotes have pointed to two distinct complexes, condensin and cohesin, as playing a central role in chromosome condensation and sister-chromatid cohesion, respectively (Hirano, Genes Dev., 1999. 13:11-19). It is believed that such regulatory complexes are not only involved in chromosome segregation but also play a fundamental role in DNA repair and dosage compensation (Hirano, Genes Dev., 1999. 13:11-19; Chaung et al., Cell, 1994. 79, 459-474). Similar to such regulatory complexes, the BRAF35/BRCA2 complex not only confers a regulatory role in progression through mitosis but also have been reported to be involved in DNA repair (Marmorstein et al., Natl. Acad Sci. 1998. USA 95:13869-13874, Chen et al., Proc. Natl. Acad. Sci. 1998. USA 95:5287-5292, Mizuta et al., Proc. Natl. Acad. Sci. 1997. USA 94:6927-6932) consistent with a dual role for this complex in modulation of DNA repair and cell cycle regulation.

It is also believed that BRCA2/BRAF35 complex modulates the components of the chromosome condensation/segregation machinery once recruited to the mitotic chromosome. Indeed, the fact that at the onset of metaphase to anaphase transition the BRAF35/BRCA2 complex can no longer be detected at the mitotic chromosomes, suggests a role for the complex in the early phases of chromosome condensation. Furthermore, the spontaneous accumulation of chromosomal abnormalities, including breaks and aberrant chromatid exchanges observed in cells from BRCA2-deficient mouse (Yu et al., Genes Dev., 2000. 14:1400-1406) may indicate a role for the complex in chromosome segregation.

The identification of BRAF35 as a structural DNA-binding component of the BRCA complex suggests a role for this complex in association with sites of unusual DNA architecture such as the ones formed during DNA recombinational repair. Such recombinational events are frequently required during the cell cycle progression (Aguilera et al., *Yeast*, 2000. 16:731-754). These results extend the proposed role for BRCA2 in DNA repair and recombination by identifying BRAF35 as a component of the complex that is believed to target it to sites of DNA damage. It is noteworthy that the human BRAF35 gene maps to chromosome sub-band 19p13.3. As loss of heterozygosity at 19p13.3 has been reported in about 50% of ovarian cancers (Wang et al., *Br. J. Cancer,* 1999. 80:70-72; Jenkins et al., *Cytogenet.* 1993. 71:76-86.), BRAF35 constitutes a candidate tumor suppressor gene in such cancers.

To determine the polypeptide composition of the BRCA2-containing complex, HeLa nuclear or S100 (a side fraction of nuclear extract preparation) extracts were chromatographed sequentially to enrich for BRCA2-containing complex. Analysis of these fractions by gel filtration chromatography revealed that BRCA2 was a component of a 2 MDa complex. DEAE-Sephacel fractions were subjected to affinity-purification using mono- and polyclonal anti-BRCA2 antibodies (Marmorstein et al, *Natl. Acad. Sci.,* 1998. USA 95:13869-13874). Western blot analysis of the affinity-eluates confirmed the presence of BRCA2 protein. Polypeptides specifically eluted from the BRCA2 affinity matrix were analyzed by matrix-assisted laser desorption/ionization time-of-flight mass spectrometry. This analysis identified among a number of proteins which were specifically enriched by the BRCA2 antibodies, a 35 kDa species, designated BRAF35 (BRCA2-associated factor), as the predicted product of the R31109 cosmid open reading frame.

BRAF35 is an evolutionary conserved protein. Expressed sequence tags containing the full-length BRAF35 protein were obtained (FIG. 1). Blast analysis using BRAF35 as the query identified a second human open reading frame with extensive homology to BRAF35, designated iBRAF35 (imitation BRAF35). This analysis also revealed *Mus musculus, Drosophila melanogaster* and *Caenorhabditis elegans* homologs of BRAF35.

Analysis of the predicted sequence of human BRAF35 indicated that it encodes a protein containing a single sequence-nonspecific HMG domain and a region with two heptad repeats similar to the coiled-coil region of kinesin.

The sequence of the nucleic acid encoding BRAF35 has also been determined and is SEQ ID NO:2.

BRAF35 is a bona fide component of the BRCA2 complex. To confirm the association of BRAF35 and BRCA2, several approaches were employed. Transient transfection of 293T cells with HA epitope tagged BRAF35 (HA-BRAF35) or control HA-XRCC2 followed by immunoprecipitation using anti-BRCA2 antibodies and Western blot analysis by anti-HA antibodies revealed the specific association of HA-BRAF35 and BRCA2. Anti-HA antibodies were used to immunoprecipitate HA-BRAF35 or HA-XRCC2, BRCA2 specifically associated with HA-BRAF35. It was also demonstrated that anti-BRCA2 antibodies can specifically precipitate BRAF35 from either HeLa or MCF7 cell extracts. Based on the known ability of these antibodies to enrich for BRCA2 (around 5-10% efficiency) (Marmorstein et al., *Proc. Natl. Acad. Sci. USA,* 1998 95:13869-13874), it is estimated that at least 2-4% of endogenous BRAF35 was present in the BRCA2 complex. Anti-BRAF35 antibodies specifically precipitated BRCA2.

BRAF35 is a component of at least two complexes and can directly interact with BRCA2. To determine the number of BRAF35-containing complexes, BRAF35 immunoreactivity was performed following a chromatographic scheme. Analysis of Superose 6 gel filtration revealed two peaks of immunoreactivity for BRAF35, a complex of approximately 2 MDa which contains BRCA2 eluted with a sharp peak in one fraction (18) and a second smaller BRAF35 complex (approximately 500 kDa) lacking BRCA2 eluting in other fractions (26-30). Therefore, BRAF35 is believed to be a component of at least two complexes displaying different molecular sizes.

To determine whether BRAF35 can directly interact with BRCA2, protein-protein interaction studies were performed using GST-BRCA2 constructs spanning the open-reading frame. This analysis revealed a specific interaction of BRAF35 with a fragment of BRCA2 spanning the amino acids 1648-2190 contained within BRC 6 through 8 of BRCA2.

To address whether cancer-causing mutations in BRCA2 disrupt the BRCA2/BRAF35 complex, the nuclear extract from CAPAN-1 cells was analyzed by Superose 6 gel filtration. CAPAN-1 cells harbor a truncation of BRCA2 (6174delT) on one allele, while the second allele is lost (Goggins et al., *Cancer Research,* 1996. 56:5360-5364). In contrast to the 2 MDa BRAF35 complex in HeLa cells, CAPAN-1 cells contained a much smaller complex at 670 kDa. Moreover, this test was unable to reliably detect the truncated BRCA2 in CAPAN-1 nuclear extract, consistent with the recent report indicating that mutations in BRCA2 result in the loss of nuclear localization signal (Spain et al., *Proc. Natl. Acad. Sci.,* 1999. USA 96:13920-13925). These results are consistent with the disruption of 2 MDa BRCA2/BRAF35 complex in CAPAN-1 nuclear extract.

BRAF35 displays a pattern of expression similar to BRCA2. Western blot analysis using anti-BRAF35 antibodies revealed the presence of BRAF35 in a wide variety of adult tissues examined with the highest levels expressed in testis and ovary. This is consistent with the expression pattern of BRCA2 (Tavtigian et al., *Nat. Genetic,* 1996. 12:333-337). Analysis of the RNA expression pattern of BRAF35 in developing mouse embryos using in situ hybridization was also done. Marked regional differences in mouse BRCA2 expression are first seen at day E11.5 of embryonic development (Sharan et al, *Nature,* 1997. 386:804-810). Thus, a comparison of mouse BRAF35 expression at E11.5 to that of BRCA2, revealed that BRAF35 displayed a nearly identical pattern of tissue expression to that of BRCA2 with highest expression observed in tissues with high mitotic index, such as the proliferating ventricular zones of the fore-, mid- and hind-brain. These results are consistent with a role for the BRAF35/BRCA2 complex in cells during mitosis.

BRAF35 decorates the early mitotic chromosomes during initiation of mitotic chromosome condensation. To directly assess the role of BRAF35 in mitotic cells, mitotic HeLa cells were examined using indirect immunofluorescence. Anti-BRAF35 antibodies stain mitotic chromosomes during early stages of chromosome condensation. This staining is coincident with the phosphorylation of serine 28 (Ser28) of histone H3, known to delineate condensed mitotic chromosomes (Goto et al., *J. Biol. Chem.* 1999. 274:25543-25549). At the onset of metaphase to anaphase, transition BRAF35 staining is no longer visible while Ser 28 phosphorylation persists.

BRAF35 is not only known to be associated with BRCA2. BRAF35 has also been shown to be associated with CoREST in a BRCA2-independent complex, where BRAF35 may be involved in neuronal-specific gene repression. In addition, BRAF35 has been associated in complex with KIAA1696 and HDAC1,2. Clearly, BRAF35 is an important component of several chromatin-modifying complexes involved in gene expression and repression.

Since BRAF35 is a component of at least two complexes one of which is lacking BRCA2, the mitotic chromosomes were analyzed using both polyclonal and monoclonal anti-BRAF35 and anti-BRCA2 antibodies. To directly analyze the chromatin associated structures, cells were stained following extraction of the soluble material by detergent treatment (Nickerson et al., *Proc. Natl. Acad. Sci.,* 1990. USA 87:2259-2263). This staining was compared to staining of condensed chromosomes using antibodies against phosphorylated forms of Ser10 (polyclonal) or Ser28 (monoclonal) of histone H3. This analysis revealed the co-localization of BRAF35 and BRCA2 on mitotic chromosomes coinciding with histone H3 phosphorylation. RAD51 was also colocalized with the BRCA2/BRAF35 complex on the mitotic chromosomes. Taken together, these results reveal a role for the BRAF35/BRCA2 complex in early phases of mitotic cell cycle progression.

The condensin complex involved in chromosome condensation was shown to display high affinity for structured DNA, such as cruciform DNA (Kimura and Hirano, *Cell,* 1997. 90:625-634). To examine the DNA-binding activity of BRAF35, a comparison of the DNA binding activity of BRAF35 to that of the BAF57 HMG domain was made (Wang et al., *Proc. Natl. Acad. Sci.,* 1998. USA 95:492-498). Recombinant BRAF35 displayed strong binding to 4WJ DNA in gel-shift assays. However, in contrast to two other sequence-specific HMG domain-containing proteins, LEF1 and mTF1, BRAF35 did not display detectable DNA binding activity when either of the duplex "arms" of the 4WJ DNA were used as probes. These results demonstrate that the DNA binding properties of BRAF35 are highly specific and similar to that of the condensin complex (Kimura and Hirano, *Cell,* 1997. 90:625-634).

Microinjection of anti-BRCA2 or anti-BRAF35 antibodies into synchronized HeLa cells causes a G2 cell cycle delay. To functionally assess the role of the BRCA2/BRAF35 complex in cell cycle progression, synchronized HeLa cell nuclei (double thymidine block) were injected with either affinity-purified anti-BRAF35 or anti-BRCA2 antibodies and the injected cells were analyzed 12 and 14 hours following release from the block. Cells were stained to identify the injected antibodies and counterstained with anti-CENP-F (Liao et al., *J. Cell Biol.,* 1995. 130:507-518). CENP-F is a reliable marker for identifying cells in G2 because it is only detected after cells have completed S phase. S phase cells that incorporate BrdU are CENP-F negative while cells that have completed S and do not incorporate BrdU are CENP-F positive. Mitotic and newly divided cells (telophase/early G1) were visually identified and counted. The IgG injected cells entered mitosis by about 10 hours and exited by 12 hours following release from the block. In contrast, analysis of anti-BRCA2 and anti-BRAF35 antibody-injected cells 12 hours following release from the block revealed a pronounced delay in entry to mitosis as evident by a three fold increase in CENP-F (G2)-positive cells. Analysis of injected cells at 14 hours indicated that more of the injected cells were able to enter mitosis, although a significant number were still delayed. Analysis of G2 cells following all three antibody treatments using anti-phosphorylated histone H3 antibodies (cells in initial phases of chromatin condensation) revealed a similar number of cells (about 5%) displaying phosphorylation of Ser 28 of histone H3. These results indicate that the impediment in entry to mitosis by injection of anti-BRCA2 and anti-BRAF35 antibodies is not due to prevention of Ser 28 phosphorylation. Taken together, these results demonstrate a role for BRCA2/BRAF35 complex in the timely progression through mitosis.

BRCA2 has now been found in a 2 MDa multiprotein complex. Through characterization of BRAF35, a bona fide DNA-binding component of the complex has been identified. It has also now been established that BRAF35 is an architectural DNA-binding protein capable of binding to cruciform DNA. The association of BRAF35 and BRCA2 with chromatin during early phases of mitotic chromosome condensation has also been shown. Through antibody microinjection experiments, a role for the complex in regulation of cell cycle progression is shown.

The interaction of BRAF35 with BRCA2 is indicative of BRAF35 also having a role in predisposition to cancers, in particular breast and ovarian cancer.

The present invention relates to the isolated nucleic acid sequence encoding BRAF35 as well as polypeptides encoded thereby. A nucleic acid sequence encoding BRAF35 (SEQ ID NO:2) and a polypeptide sequence of BRAF35 is depicted in FIG. 1 (SEQ ID NO:1) are provided. Using these sequences, antibodies, including both polyclonal and monoclonal antibodies, can be raised which bind selectively to BRAF35. Both polyclonal and monoclonal antibodies against BRAF35 can be raised routinely in accordance with well established methods.

The antibodies of the present invention can be detectably labeled with, for example, a fluorophore or radiolabel, and used to detect cancers, particularly breast or ovarian cancer.

Antibodies of the present invention can also be used to detect DNA damage in cells. By DNA damage it is meant to include, but is not limited to mutations in the nucleic acid sequence encoding BRAF35 and DNA damage which leads to mutations in the BRAF35 protein. In this method, cells are contacted with anti-BRAF35 antibodies. The ability of the antibodies to bind with BRAF35 protein is then determined. DNA damage to the cell results in decreased antibody binding. As will be understood by those of skill in the art upon reading this disclosure, however, other means for detecting DNA damage including, but not limited to, screening of patient DNA samples for mutations can be used. Methods for comparing a DNA sample obtained from an individual with the nucleic acid sequence for BRAF35 (SEQ ID NO:2) to identify individuals with mutations in this nucleic acid sequence can be performed routinely in accordance with known methods. Individuals identified as having a mutant BRAF35 gene or encoding mutant BRAF35 proteins are believed to have a predisposition to development of cancer, in particular breast and ovarian cancer.

The role of the multiprotein BRAF35/BRCA2 complex of the present invention in regulating cell cycle progression also provides a means for identifying agents which regulate cell cycle progression and using these agents to regulate cell cycle progression in cells expressing BRAF35 or BRCA2. Agents which interfere with the interaction and/or function of the BRCA2/BRAF35 complex are believed to be useful in the treatment of cancer.

Accordingly, the present invention also relates to methods and compositions for the treatment of cancer, particularly breast and ovarian cancer. In one embodiment, compositions of the present invention comprise an agent which interferes with the interaction and/or function of BRAF35 with BRCA2. In another embodiment, tumor growth is suppressed by supplying BRAF35 to a tumor site. BRAF35 can be supplied at the tumor site via administration of the BRAF35 protein or via administration of a vector and/or host cells comprising a nucleic acid sequence encoding the BRAF35 protein.

The invention is further illustrated by the following, non-limiting examples.

EXAMPLES

Example 1

Affinity Purification of BRCA2 from Nuclear or S100 Extract

Affinity purification of BRCA2 associated polypeptides was performed using either mono- or poly-clonal anti-BRCA2 antibodies. Antibodies were coupled to 1 ml protein A agarose beads (Repligen) in accordance with known techniques. The resin was incubated overnight at 4° C. with 10 mg HeLa DEAE-Sephacel precleared with 1 ml protein A beads. Binding was carried out in NEBB buffer (250 mM NaCl, 30 mM Tris 7.6, 10% glycerol, 0.1 mM EDTA, 5 mM BME, 0.2 mM PMSF, 0.1% NP-40) The support was then washed successively with NEBB buffer containing 500 mM NaCl, 0.1% NP-40; 500 mM NaCl, 0.5% NP-40; 1.0 M NaCl, 0.1% NP-40; and 20 mM NaCl, 1.0% NP-40. The washed beads were then eluted with three column volumes of 100 mM glycine, pH 3.0.

Example 2

Conventional Purification of the BRCA2 Complex

BRCA2 was purified from 1.2 grams of HeLa nuclear extract. Nuclear extract was loaded on a 200 ml column of phosphocellulose (P11, Whatman) and fractionated stepwise by the indicated KCl concentrations in buffer A (20 mM Tris.HCl, pH 7.9, 0.2 mM EDTA, 10 mM, 10% glycerol, 0.2 mM PMSF). The P11 0.5 M KCl fraction (200 mg) was loaded on a 20 ml DEAE-Sephacel column (Pharmacia) and eluted with 0.35 M KCl elution (10 mg) was dialyzed to 100 mM KCl in buffer A and loaded on a MonoS 5/5 column (Pharmacia). The column was resolved using a linear 10 column volume gradient of 100 to 650 mM KCl. Fractions containing BRCA2 (500 mM KCl, 0.5 mg) were dialyzed to 700 mM KCl, 0.1% NP-40 in buffer A and loaded on a Superose 6 HR 10/30 (Pharmacia) equilibrated in the same buffer containing aprotinin, leupeptin, and pepstatin.

Example 3

Gel-Shift Assays

The 4WJ DNA and its duplex DNA arms were prepared according to Bianchi (Bianchi at el., *Science*, 1989. 243: 1056-1059). Binding reactions were performed as described (West et al., *Nucleic Acids Research*, 1999. 27:984-992). Full length BRAF35 was prepared similar to that described for BAF57 (Wang et al., *Proc. Natl. Acad. Sci.*, 1998. USA 95:492-498).

Example 4

In Situ Hybridization

Radioactive in situ hybridization was performed as described (Lutz et al., *Development*, 1994. 120: 25-36) using antisense probes prepared from EST AA007769 (BRAF35) and AA571559 (BRCA2) and 8 μM sections of paraffin embedded embryos after fixation in 4% paraformaldehyde and dehydration. Slides were coated with photographic emulsion, exposed for 5-10 days, counterstained with Hoechst 33258 nuclear dye and photographed using dark field and fluorescent illumination. Figures were processed using Adobe Photoshop software.

Example 5

Immunoprecipitation and Immunofluorescence

Transient transfection assays and immunoprecipitation experiments were performed in accordance with known methods (Marmorstein et al., *Proc. Natl. Acad. Sci.*, 1998. USA 95:13869-13874). Briefly, cell lysate were prepared using lysis buffer containing 50 mM Tris-HCl, pH 8.0, 120 mM NaCl, 1 mM EDTA, 0.5% NP 40 and 1× complete proteinase inhibitor (Boehringer Mannheim). The total protein content of the lysate was determined. 2 mg of whole cell extract was diluted in 1 ml of the lysis buffer and incubated with different antibodies following which protein A agarose beads were added and the mix was incubated at cold for 1 hour. Following centrifugation, pellets were washed and resuspended in protein sample buffer and boiled for 5 minutes. Eluates were separated by SDS-PAGE and transferred onto a polycvinylidence difluoride membrane (Millipore). ECL (Amersham) was used for signal detection.

Immunofluorescence experiments were performed using monoclonal and polyclonal antibodies against BRCA2 and BRAF35 (Yarden and Brody, *Proc. Natl. Acad. Sci.*, 1999. USA 96:4983-4988). Cells grown on coverslips are washed with ice-cold PBS twice, then treated with ice-cold cytoskeleton buffer containing: 10 mM PIPES pH 6.8, 100 mM NaCl, 300 mM sucrose, 3 mM MgCl2, 1 mM EGTA, 0.5% triton X-100. After five minutes on ice, cells were aspirated and were treated with ice-cold stripping buffer containing: 10 mM Tris-HCl pH 7.4, 10 mM NaCl, 3 mM MgCl2, 1% Tween 40 (v/v), 0.5% sodium deoxycholate (v/v) for 5 minutes. Cells were then washed three times with ice-cold PBS and fixed in modified Streck tissue fixative (150 mM 2-bromo-2-nitro-1, 3-propanediol (Sigma), 108 mM diazolidinyl urea (Sigma), 10 mM Na Citrate, 50 mM EDTA pH 5.7) for 30 minutes at room temperature. Following fixation cells are washed in PBS and permeabilized for 15 minutes using 100 mM Tris-HCl pH 7.4, 50 mM EDTA and 0.5% Triton X-100. Cells are then blocked using 10% FCS in PBS and 0.1% azide and incubated with the primary and secondary antibodies.

Monoclonal anti-BRCA2 antibodies (4.56 and 5.23) were raised against a BRCA2 fusion protein encoding amino acids 2959-3418. Monoclonal antibodies were also developed to a BRAF35 fusion protein (amino acids 103-317). Polyclonal antibodies were also developed against the last twenty amino acids of BRCA2 (C20) and BRAF35 and the first twenty amino acid of BRAF35 (Poly (N)). All polyclonal antibodies were affinity-purified using the appropriate peptides. Antibody against HA was obtained from Santa Cruz Biotechnology. Antibodies against phosphorylated S10 and S28 were purchased through UBI and Sigma, respectively.

Example 6

GST-BRCA2 Fusion Proteins and GST Pull-Down Experiments

GST-BRCA2 fusion protein constructs were obtained. GST-BRCA2 fusion proteins #1 to #7 correspond to amino acids 195-784, 705-1217, 1171-1658, 1648-2190, 2114-2608, 2634-2999 and 2959 to 3418, respectively. GST and GST-BRCA2 (pGEX, Amersham Pharmacia) fusion proteins were expressed in *E. coli* BL21. Cells were harvested and lysed by sonicated in 150 mM NaCl in Buffer G (50 mM Tris, pH 8.0, 10% glycerol, 0.5% Triton X-100, 0.5 mM PMSF, 1 ug/ml aprotinin, 1 ug/ml leupeptin, and 1 ug/ml pepstatin). The cell lysates were cleared by centrifugation (105,000×g for 60 minutes at 4° C. Concentration of GST or GST-BRCA2 fusion proteins in cell lysates was determined by estimation of protein concentration by Coomassie staining of SDS-PAGE samples purified by affinity chromatography on glutathione-Sepharose (Amersham Pharmacia). Cell lysates containing GST-BRCA2 fusion protein were mixed with glutathione-Sepharose, incubated for 3 hours at 4° C., and washed three times each with 150 mM NaCl, 500 mM NaCl, and 150 mM NaCl in Buffer G. Over-expressed *E. coli* BRAF35 (pet-28b, Novagen) lysate was added and beads were incubated for 3 hours at 4° C. Beads were washed two times each with 300 mM NaCl, and 150 mM NaCl in Buffer G, and eluted with 30 mM glutathione plus 150 mM NaCl in Buffer G. Samples were subjected to SDS-PAGE followed by Western blotting to determine the presence of BRAF35.

Example 7

Antibody Microinjection Experiments

Hela cells plated on No. 1 coverslips were synchronized by a double thymidine block. Rabbit anti-BRCA2, BRAF35 and non-immune antibodies were concentrated to approximately 5 mg/ml in PBS and injected into nuclei of cells 30 to 60 minutes following release form the block using an Eppendorf semi-automated microinjector and manipulator mounted on a Nikon TE300 inverted microscope. Samples were taken at 12 to 14 hours after release from the G1/S boundary when neighboring uninjected or cells injected with non-immune IgG had mostly exited mitosis. Cells were fixed in 3.7% paraformaldehyde/PBS for 8 minutes, permeabilized in 0.2% Triton X100/PBS/0.1% BSA for 5 minutes, washed in PBS/0.1% BSA and stained. Injected antibodies were detected with FITC anti-rabbit secondary antibodies (Jackson Immunoresearch). Cells were also co-stained with VD human autoimmune serum to detect CENP-F (Rattner et al., *Cell Mot. Cytosk.*, 1993. 26:214-226), rat anti-phospho Ser10 H3 and visualized with Cy5 conjugated anti-human (Jackson Immunoresearch) and Alexa594 conjugated anti-rat secondary antibodies (Molecular Probes), respectively. Coverslips were visualized with a Nikon Microphot upright microscope with a 100× objective and images were captured with a 8 bit CCD camera driven by Signal Analytics image processing program.

What is claimed is:

1. An affinity purified and isolated multiprotein complex comprising a BRCA2 protein and a BRAF35 protein, wherein the amino acid sequence of the BRAF35 protein comprises SEQ ID NO:1, and wherein antibody efficiency of affinity purification of the BRCA2 protein of the affinity purified multiprotein complex is at 5 to 10%.

* * * * *

SEQUENCE LISTING

<160> NUMBER OF SEQ ID NOS: 2

<210> SEQ ID NO 1
<211> LENGTH: 317
<212> TYPE: PRT
<213> ORGANISM: Homo sapiens

<400> SEQUENCE: 1

```
Met Ser His Gly Pro Lys Gln Pro Gly Ala Ala Ala Ala Pro Ala Gly
1               5                   10                  15

Gly Lys Ala Pro Gly Gln His Gly Gly Phe Val Val Thr Val Lys Gln
                20                  25                  30

Glu Arg Gly Glu Gly Pro Arg Ala Gly Glu Lys Gly Ser His Glu Glu
            35                  40                  45

Glu Pro Val Lys Lys Arg Gly Trp Pro Lys Gly Lys Lys Arg Lys Lys
        50                  55                  60

Ile Leu Pro Asn Gly Pro Lys Ala Pro Val Thr Gly Tyr Val Arg Phe
65                  70                  75                  80

Leu Asn Glu Arg Arg Glu Gln Ile Arg Thr Arg His Pro Asp Leu Pro
                85                  90                  95

Phe Pro Glu Ile Thr Lys Met Leu Gly Ala Glu Trp Ser Lys Leu Gln
                100                 105                 110

Pro Thr Glu Lys Gln Arg Tyr Leu Asp Glu Ala Glu Arg Glu Lys Gln
            115                 120                 125

Gln Tyr Met Lys Glu Leu Arg Ala Tyr Gln Gln Ser Glu Ala Tyr Lys
        130                 135                 140

Met Cys Thr Glu Lys Ile Gln Glu Lys Lys Ile Lys Lys Glu Asp Ser
145                 150                 155                 160

Ser Ser Gly Leu Met Asn Thr Leu Leu Asn Gly His Lys Gly Gly Asp
                165                 170                 175

Cys Asp Gly Phe Ser Thr Phe Asp Val Pro Ile Phe Thr Glu Glu Phe
            180                 185                 190

Leu Asp Gln Asn Lys Ala Arg Glu Ala Glu Leu Arg Arg Leu Arg Lys
        195                 200                 205
```

```
Met Asn Val Ala Phe Glu Glu Gln Asn Ala Val Leu Gln Arg His Thr
    210                 215                 220

Gln Ser Met Ser Ser Ala Arg Glu Arg Leu Glu Gln Glu Leu Ala Leu
225                 230                 235                 240

Glu Glu Arg Arg Thr Leu Ala Leu Gln Gln Leu Gln Ala Val Arg
                245                 250                 255

Gln Ala Leu Thr Ala Ser Phe Ala Ser Leu Pro Val Pro Gly Thr Gly
                260                 265                 270

Glu Thr Pro Thr Leu Gly Thr Leu Asp Phe Tyr Met Ala Arg Leu His
            275                 280                 285

Gly Ala Ile Glu Arg Asp Pro Ala Gln His Glu Lys Leu Ile Val Arg
    290                 295                 300

Ile Lys Glu Ile Leu Ala Gln Val Ala Ser Glu His Leu
305                 310                 315

<210> SEQ ID NO 2
<211> LENGTH: 1318
<212> TYPE: DNA
<213> ORGANISM: Homo sapiens

<400> SEQUENCE: 2
cggagcggat gtcccacggc cccaagcagc ccggcgcggc cgccgcgccg gcgggcggca      60
aggctccggg ccagcatggg ggcttcgtgg tgactgtcaa gcaagagcgc ggcgagggtc     120
cacgcgcggg cgagaagggg tcccacgagg aggagccggt gaagaaacgc ggctggccca     180
agggcaagaa gcggaagaag attctgccga atgggcccaa gcaccggtc acgggctacg      240 tgcgcttcct gaacgagcgg cgcgagcaga tccgcacgcg ccacccggat ctgcccttc     300 ccgagatcac caagatgctg ggcgccgagt ggagcaagct gcagccaacg gaaaagcagc     360
ggtacctgga tgaggccgag agagagaagc agcagtacat gaaggagctg cgggcgtacc     420
agcagtctga agcctataag atgtgcacgg agaagatcca ggagaagaag atcaagaaag     480
aagactcgag ctctgggctc atgaacactc tcctgaatgg accacaaggg tggggactgc     540
gatggcttct ccaccttcga tgttcccatc ttcactgaag agttcttgga ccaaaacaaa     600
gcgcgtgagg cggagcttcg gcgcttgcgg aagatgaatg tggccttcga ggagcagaac     660
gcggtactgc agaggcacag cagagcatga gcagcgcgcg cgagcgtctg gagcaggagc     720
tggcgctgga ggagcggagg acgctggcgc tgcagcagca gctccaggcc gtgcgccagg     780
cgctcaccgc cagcttcgcc tcactgccgg tgccgggcac gggcgaaacg cccacgctgg     840
gcactctgga cttctacatg gcccggcttc acggagccat cgagcgcgac cccgcccagc     900
acgagaagct catcgtccgc atcaaggaaa tcctggccca ggtcgccagc gagcaccttg     960
aggagtgggc gggcccacga tgcagaggag aagctgtggg cgcgcggccc tgccacaccc    1020
caccccgtgg acgagaggct gggggtccac cctttgggc ctggtcccat cctgcacctt    1080
gggggctcca gccccttaa aattaaattt ctgcagcatc cctttagctt tcaatctccc    1140 cagcccctg aacccggaaa aagcactcgc tgcgcgatac acccagaaga acctcacagc    1200
cagggtgccc ctcctcggag gacagccacg cgctacactg gctctccggg ccacccccag    1260
gacacagggc agacgaaacc cacccccagc acacggcagg acccccaaa ttactcac      1318
```